June 15, 1943. F. MEILLAND Plant Pat. 591
ROSE PLANT
Filed July 15, 1942
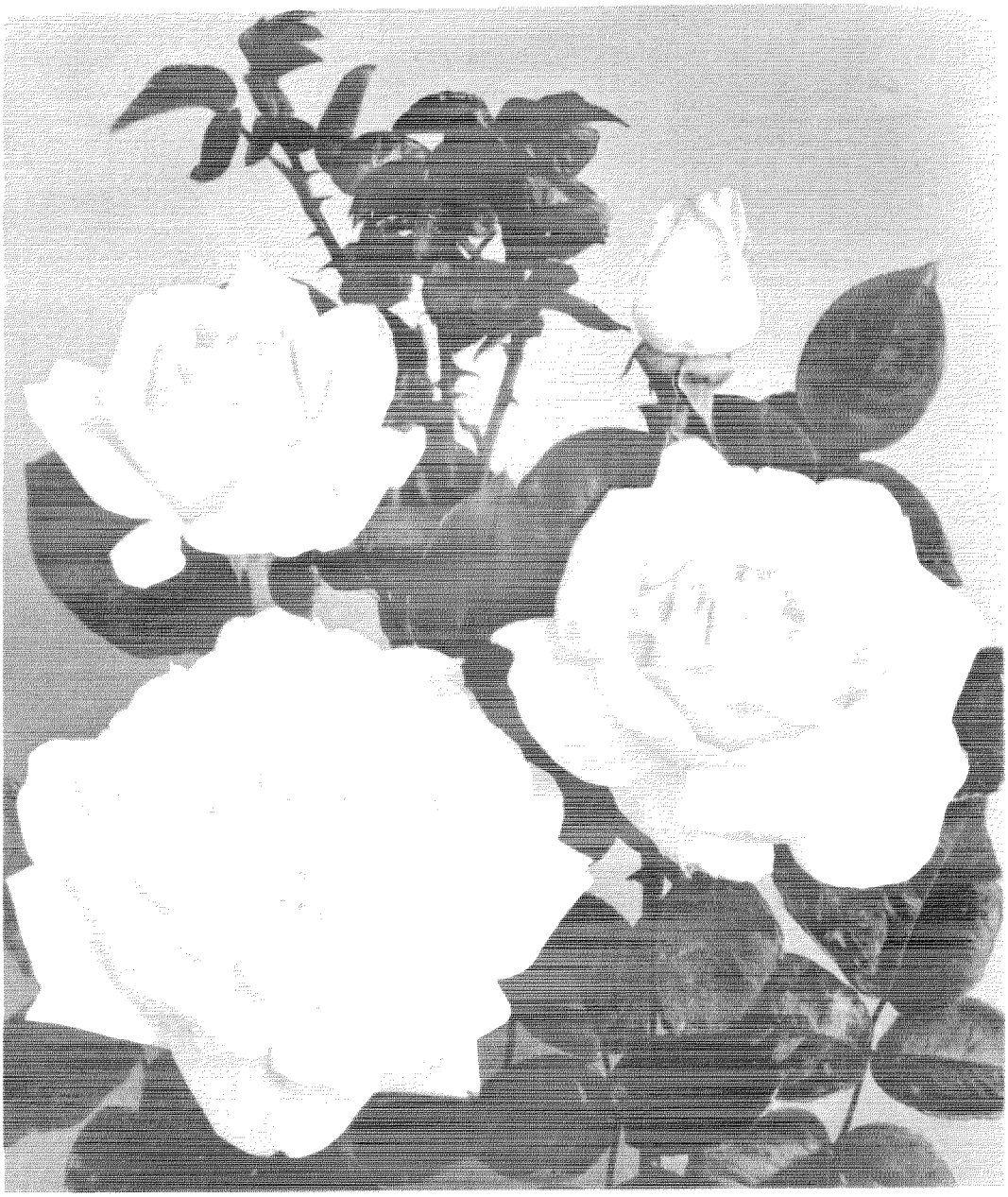
Inventor
Francis Meilland
By Robert Robb
Attorney Patented June 15, 1943

UNITED STATES PATENT OFFICE

591

ROSE PLANT

Francis Meilland, Tassin-les-Lyon, France, assignor to The Conrad-Pyle Company, West Grove, Pa.

Application July 15, 1942, Serial No. 451,039

1 Claim. (Cl. 47—61)

The present invention relates to a new and distinct variety of hybrid tea rose plant, a seedling resulting from a definite effort to produce an improvement in this class of roses.

The primary features of this new variety which connote its distinctive advance over existing types are the exceptional vigor and enduring quality of its foliage and the character of its bloom, first in respect to its size; second, its perfection of form; and third, with respect to its exquisite blend of coloring, more particularly apparent in the accompanying illustration of a specimen thereof.

The following is a detail description of the new variety, color terminology being in accord with Ridgway's Color Standard:

Type: Hardy; bush; outdoor; seedling; for cut flowers and garden decoration.

Class: Hybrid tea.

Propagation: Holds its distinguishing characteristics through succeeding propagations by budding.

*Flower*

Locality where grown: West Grove, Pennsylvania.

Flowers borne: Singly to stem on strong, medium long stems.

Quantity of bloom: Abundant outdoors.

Continuity: Intermittent, almost continuous.

Fragrance: Moderate; tea.

Bud:

*Peduncle.*—Medium long; heavy; erect; stiff; Dark Citrine, Plate IV; rough. Prickles—moderately few, Garnet-Brown, Plate I.

*Before calyx breaks.—Size*—large. *Form*—globular with an inconspicuous neck; with foliaceous appendages on the surface of the bud; with bristle-like foliaceous parts extending beyond the tip of the bud equal to about one-fourth of its length.

*As calyx breaks.*—Pale Lemon Yellow, Plate IV, flushed with Nopal Red, Plate I.

*As first petal opens.—Size*—large. *Form*—ovoid. *Color*—Outside—Lemon Yellow base to Martius Yellow edge, Plate IV. Inside—Lemon Yellow base to Martius Yellow edge, Plate IV, and tipped Shrimp Pink, Plate I. *Opening*—opens up well.

Bloom:

*Size when fully open.*—Large; five to five and one-half inches.

*Petalage.*—Very double; from fifty to fifty-five petals arranged regularly.

*Form.—Cupped*; high centers; globular at first; becoming cupped and high centered; petals remaining at first tightly rolled inward; becoming later, at maturity, loosely rolled outward.

Petals: Leathery; inside and outside satiny.

*Shape.*—Outside—oval; scalloped with apex flat with one notch. Intermediate—ovate; scalloped with one notch. Inside—ovate; scalloped with one notch.

This description of a newly opened flower was made from a rose grown outdoors during the month of November, 1941, at West Grove, Pennsylvania.

*Color.—Outside petal*—Outside surface—Lemon Yellow base to Martius Yellow, Plate IV, edged Rose Pink, Plate XII. Inside surface—Lemon Yellow base to Martius Yellow, Plate IV, edged Rose Pink, Plate XII. *Intermediate petal*—Outside surface—Lemon Yellow base to Martius Yellow, Plate IV, edged Rose Pink, Plate XII. Inside surface—Lemon Yellow base to Martius Yellow, Plate IV, edged Rose Pink, Plate XII. *Inner petal*—Outside surface—Lemon Yellow base to Martius Yellow, Plate IV, edged Rose Pink, Plate XII. Inside surface—Lemon Yellow base to Martius Yellow, Plate IV, edged Rose Pink, Plate XII.

This description was made from a rose that was open for three days outdoors, in November, 1941, at West Grove, Pennsylvania:

*Color.—Outside petal*—Outside surface—Lemon Yellow base to Martius Yellow, Plate IV, edged Rose Pink, Plate XII. Inside surface—Lemon Yellow base to Martius Yellow, Plate IV, edged Rose Pink, Plate XII. *Inside petal*—Outside surface—Lemon Yellow base to Martius Yellow, Plate IV, edged Rose Pink, Plate XII. Inside surface—Lemon Yellow base to Martius Yellow, Plate IV, edged Rose Pink, Plate XII.

*General color effect.*—Newly opened flower—Martius Yellow, Plate IV. Three days open—Martius Yellow, Plate IV.

*Behavior.*—Drop off cleanly; do not fade.

*Flower longevity.*—On bush in garden four to five days in November. Cut roses grown outdoors kept at living room temperatures four to six days in November.

*Reproductive organs*

Stamens: Many; arranged irregularly.

Filaments: Short and long; Nopal Red, Plate I; most with anthers.

Anthers: Medium size; Light Orange Yellow, Plate III; open at various times.

Pollen: Abundant; Capucine Yellow.

Pistils: Many.

Styles: Medium length; thin; bunched.

Stigma: Straw Yellow, Plate XVI.

Ovaries: All enclosed in calyx.

Hips: Short; pointed; with inconspicuous neck; pear-shaped; Bice Green, Plate XVII; smooth; walls thick, fleshy.

Sepals: Falling soon; moderately long; spear-shaped; recurved.

Seeds: Few; medium large.

*Plant*

Foliage:

*Leaves.*—Compound of five leaflets; normal; large; leathery; glossy.

*Leaflets.*—Ovoid with apex acute; base round; margin serrate.

Color.—*Mature*—Upper surface—Dark Varleys Green, Plate XVIII. Under surface—Light Elm Green, Plate XVII. *Young*—Upper surface—Roman Green, Plate XVI, veiled with Claret-Brown, Plate I. Under surface—Varleys Green, Plate XVIII, shaded Claret-Brown, Plate I.

*Rachis.*—Medium heavy; upper side, smooth, grooved; under side, sparsely thorny.

*Stipules.*—Medium long; medium wide; moderately long points, turning out at an angle of less than 45°, recurved toward the stem.

*Disease.*—Resistant to mildew and blackspot.

Growth:

*Habit.*—Upright; much branched.

*Growth.*—Vigorous.

*Canes.*—Moderately heavy.

*Main stems.*—Dull Cedar Green, Plate VI. *Thorns*—several; medium long; straight; hooked downward; with narrow base. *Prickles*—none. *Hairs*—none.

*Branches.*—Dull Cedar Green, Plate VI. *Thorns*—several; medium long; hooked downward; with narrow base. *Prickles*—none. *Hairs*—none.

*New shoots.*—Bright Victoria-Lake, Plate I. *Thorns*—many; medium long; hooked downward; with narrow base. *Prickles*—none. *Hairs*—none.

I claim:

A new and distinct variety of rose plant of the hybrid tea class, characterized as to novelty by its exceptionally vigorous growing habit and enduring quality of its foliage, size and perfection of form of the bloom, and their unusual blend of coloring, substantially as shown and described.

FRANCIS MEILLAND.

CERTIFICATE OF CORRECTION.

Plant Patent No. 591. June 15, 1943.

FRANCIS MEILLAND.

It is hereby certified that the name of the assignee in the above numbered patent was erroneously described and specified as "The Conrad-Pyle Company" whereas said name should have been described and specified as --The Conard-Pyle Company--; and that the said Letters Patent should be read with this correction therein that the same may conform to the record of the case in the Patent Office.

Signed and sealed this 23rd day of May, A. D. 1944.

Leslie Frazer

(Seal) Acting Commissioner of Patents.

Hips: Short; pointed; with inconspicuous neck; pear-shaped; Bice Green, Plate XVII; smooth; walls thick, fleshy.

Sepals: Falling soon; moderately long; spear-shaped; recurved.

Seeds: Few; medium large.

*Plant*

Foliage:

*Leaves.*—Compound of five leaflets; normal; large; leathery; glossy.

*Leaflets.*—Ovoid with apex acute; base round; margin serrate.

Color.—*Mature*—Upper surface—Dark Varleys Green, Plate XVIII. Under surface—Light Elm Green, Plate XVII. *Young*—Upper surface—Roman Green, Plate XVI, veiled with Claret-Brown, Plate I. Under surface—Varleys Green, Plate XVIII, shaded Claret-Brown, Plate I.

*Rachis.*—Medium heavy; upper side, smooth, grooved; under side, sparsely thorny.

*Stipules.*—Medium long; medium wide; moderately long points, turning out at an angle of less than 45°, recurved toward the stem.

*Disease.*—Resistant to mildew and blackspot.

Growth:

*Habit.*—Upright; much branched.

*Growth.*—Vigorous.

*Canes.*—Moderately heavy.

*Main stems.*—Dull Cedar Green, Plate VI. *Thorns*—several; medium long; straight; hooked downward; with narrow base. *Prickles*—none. *Hairs*—none.

*Branches.*—Dull Cedar Green, Plate VI. *Thorns*—several; medium long; hooked downward; with narrow base. *Prickles*—none. *Hairs*—none.

*New shoots.*—Bright Victoria-Lake, Plate I. *Thorns*—many; medium long; hooked downward; with narrow base. *Prickles*—none. *Hairs*—none.

I claim:

A new and distinct variety of rose plant of the hybrid tea class, characterized as to novelty by its exceptionally vigorous growing habit and enduring quality of its foliage, size and perfection of form of the bloom, and their unusual blend of coloring, substantially as shown and described.

FRANCIS MEILLAND.

CERTIFICATE OF CORRECTION.

Plant Patent No. 591. June 15, 1943.

FRANCIS MEILLAND.

It is hereby certified that the name of the assignee in the above numbered patent was erroneously described and specified as "The Conrad-Pyle Company" whereas said name should have been described and specified as --The Conard-Pyle Company--; and that the said Letters Patent should be read with this correction therein that the same may conform to the record of the case in the Patent Office.

Signed and sealed this 23rd day of May, A. D. 1944.

Leslie Frazer

(Seal) Acting Commissioner of Patents.